(12) United States Patent
Davey et al.

(10) Patent No.: US 12,268,802 B2
(45) Date of Patent: Apr. 8, 2025

(54) OXYGENATOR FOR USE WITH EXTRACORPOREAL SUPPORT OF PREMATURE FETUS

(71) Applicant: THE CHILDREN'S HOSPITAL OF PHILADELPHIA, Philadelphia, PA (US)

(72) Inventors: Marcus Graeme Davey, Philadelphia, PA (US); Alan Flake, Philadelphia, PA (US)

(73) Assignee: The Children's Hospital of Philadelphia, Philadelphia, PA (US)

(*) Notice: Subject to any disclaimer, the term of this patent is extended or adjusted under 35 U.S.C. 154(b) by 713 days.

(21) Appl. No.: 17/603,173

(22) PCT Filed: Apr. 8, 2020

(86) PCT No.: PCT/US2020/027137
§ 371 (c)(1),
(2) Date: Oct. 12, 2021

(87) PCT Pub. No.: WO2020/210275
PCT Pub. Date: Oct. 15, 2020

(65) Prior Publication Data
US 2022/0193318 A1 Jun. 23, 2022

Related U.S. Application Data

(60) Provisional application No. 62/831,311, filed on Apr. 9, 2019.

(51) Int. Cl.
*A61M 1/16* (2006.01)
*A61G 11/00* (2006.01)
*A61M 1/36* (2006.01)

(52) U.S. Cl.
CPC .......... *A61M 1/1698* (2013.01); *A61G 11/00* (2013.01); *A61M 1/3623* (2022.05); *A61M 1/3666* (2013.01); *A61M 2240/00* (2013.01)

(58) Field of Classification Search
CPC .............. A61M 1/1698; A61M 1/3623; A61M 1/3666; A61M 2240/00; A61G 11/00
See application file for complete search history.

(56) References Cited

U.S. PATENT DOCUMENTS

| | | | | |
|---|---|---|---|---|
| 3,998,593 A | * | 12/1976 | Yoshida | B01D 63/082 96/6 |
| 4,749,551 A | | 6/1988 | Borgione | |
| 6,387,323 B1 | * | 5/2002 | Afzal | A61M 60/232 604/6.14 |
| 6,602,467 B1 | * | 8/2003 | Divino, Jr. | B01F 23/23413 604/4.01 |

(Continued)

*Primary Examiner* — Susan S Su
*Assistant Examiner* — Erin A Kim
(74) *Attorney, Agent, or Firm* — BakerHostetler

(57) ABSTRACT

Disclosed are devices and methods directed to oxygenators for use in extracorporeal circuits for supporting a fetus. An oxygenator for use with an extracorporeal circuit includes a housing defining a cavity therein and a gas exchanger disposed within the interior cavity. The cavity is configured to receive blood a fetus. The gas exchanger is configured to receive a sweep gas and further configured to contact the blood within the cavity, such that at least oxygen gas and carbon dioxide gas is permitted to diffuse between the blood and the gas exchanger.

24 Claims, 8 Drawing Sheets

(56) References Cited

U.S. PATENT DOCUMENTS

| | | | |
|---|---|---|---|
| 2007/0010005 A1* | 1/2007 | Sitzmann | A61M 1/36 435/283.1 |
| 2008/0199357 A1* | 8/2008 | Gellman | A61M 1/3623 604/6.14 |
| 2015/0314059 A1 | 11/2015 | Federspiel et al. | |
| 2016/0022524 A1* | 1/2016 | Flake | A61M 1/3623 600/22 |
| 2016/0095969 A1 | 4/2016 | Maurer et al. | |
| 2017/0100531 A1* | 4/2017 | Madhani | B01D 63/02 |
| 2018/0078695 A1* | 3/2018 | Plott | B01D 63/02 |
| 2018/0126057 A1* | 5/2018 | Steffens | A61M 1/3623 |
| 2018/0168901 A1 | 6/2018 | Flake et al. | |
| 2019/0009015 A1* | 1/2019 | Ahrens | A61M 1/1698 |
| 2019/0380900 A1* | 12/2019 | Flake | A61M 1/3621 |
| 2020/0188568 A1* | 6/2020 | Gipson | A61M 1/1698 |

\* cited by examiner

OXYGENATOR FOR USE WITH EXTRACORPOREAL SUPPORT OF PREMATURE FETUS

CROSS-REFERENCE TO RELATED APPLICATIONS

This application is the National Stage Application of International Patent Application No. PCT/US2020/027137, filed Apr. 8, 2020, which claims the benefit of U.S. Provisional Application No. 62/831,311, filed Apr. 9, 2019, the entirety of which is incorporated herein for any and all purposes.

TECHNICAL FIELD

This disclosure generally relates to devices and methods of providing gas exchange for premature fetuses in an artificial womb system, and more particularly relates to a new design for an oxygenator for use within an extracorporeal circuit for supporting a premature fetus.

BACKGROUND

Extreme prematurity is the leading cause of infant morbidity and mortality in the United States, with over one third of all infant deaths and one half of cerebral palsy diagnoses attributed to prematurity. The 2010 Center for Disease Control National Vital Statistics Report notes birth rates at a gestational age of less than 28 weeks in the United States over roughly the past decade have remained stable at approximately 0.7%, or 30,000 births annually. Similarly, birth rates at gestational ages 28-32 weeks over the past decade in the United States have been stable at 1.2%, or 50,000 births annually.

Premature birth may occur due to any one of a multitude of reasons. For example, premature birth may occur spontaneously due to preterm rupture of the membranes (PROM), structural uterine features such as shortened cervix, secondary to traumatic or infectious stimuli, or due to multiple gestation. Preterm labor and delivery is also frequently encountered in the context of fetoscopy or fetal surgery, where instrumentation of the uterus often stimulates uncontrolled labor despite maximal tocolytic therapy.

Respiratory failure represents the most common and challenging problem associated with extreme prematurity, as gas exchange in critically preterm neonates is impaired by structural and functional immaturity of the lungs. Advances in neonatal intensive care have achieved improved survival and pushed the limits of viability of preterm neonates to 22 to 24 weeks gestation, which marks the transition from the canalicular to the saccular phase of lung development. Although survival has become possible, there is still a high rate of chronic lung disease and other complications of organ immaturity, particularly in fetuses born prior to 28 weeks gestation. The development of a system that could support normal fetal growth and organ maturation for even a few weeks could significantly reduce the morbidity and mortality of extreme prematurity, and improve quality of life in survivors.

The development of an "artificial placenta" has been the subject of investigation for over 50 years with little success. Previous attempts to achieve adequate oxygenation of the fetus in animal models have employed traditional extracorporeal membrane oxygenation (ECMO) with pump support, and have been limited by circulatory overload and cardiac failure in treated animals. Furthermore, to operate existing systems, the oxygenators have to be primed with a larger-than-desired priming volume to function properly. Due to the differences in size and blood composition of fetuses, such required volumes negatively affect the fetus and result in dilution of the fetal blood. The known systems have suffered from unacceptable complications, including: 1) progressive circulatory failure due to after-load or pre-load imbalance imposed on the fetal heart by oxygenator resistance or by circuits incorporating various pumps; and 2) hemodilution due to large priming volumes requires to operate existing oxygenators.

Accordingly, a system and method configured to provide extracorporeal support for a premature fetus, or fetuses (preterm or term) with inadequate respiratory gas exchange to support life, due to a spectrum of conditions/disorders, may improve viability. There is a need for an improved oxygenator that allows for decreased resistance to blood flow through the oxygenator and can function properly with a smaller priming volume.

SUMMARY

The foregoing needs are met by the various aspects of oxygenators, oxygenation circuits, and extracorporeal support systems disclosed. According to an aspect of this disclosure, an oxygenator for use with an extracorporeal circuit includes a housing defining a cavity therein and a gas exchanger disposed within the interior cavity. The cavity is configured to receive blood a fetus. The gas exchanger is configured to receive a sweep gas and further configured to contact the blood within the cavity, such that at least oxygen gas and carbon dioxide gas is permitted to diffuse between the blood and the gas exchanger.

According to an aspect of this disclosure, an extracorporeal system for supporting a fetus includes a chamber configured to receive the fetus, an oxygenator operatively connected to the fetus and configured to provide a gas exchange to blood from the fetus, and a heating element configured to maintain a desired temperature of the system.

BRIEF DESCRIPTION OF THE DRAWINGS

The present application is further understood when read in conjunction with the appended drawings. For the purpose of illustrating the subject matter, there are shown in the drawings exemplary embodiments of the subject matter; however, the presently disclosed subject matter is not limited to the specific methods, devices, and systems disclosed. In the drawings.

Aspects of the disclosure will now be described in detail with reference to the drawings, wherein like reference numbers refer to like elements throughout, unless specified otherwise.

DETAILED DESCRIPTION OF ILLUSTRATIVE EMBODIMENTS

Aspects of the disclosure will now be described in detail with reference to the drawings, wherein like reference numbers refer to like elements throughout, unless specified otherwise. Certain terminology is used in the following description for convenience only and is not limiting. The term "plurality", as used herein, means more than one. The terms "a portion" and "at least a portion" of a structure include the entirety of the structure. Certain features of the disclosure which are described herein in the context of separate embodiments may also be provided in combination in a single embodiment. Conversely, various features of the disclosure that are described in the context of a single embodiment may also be provided separately or in any sub combination.

Figure 1:
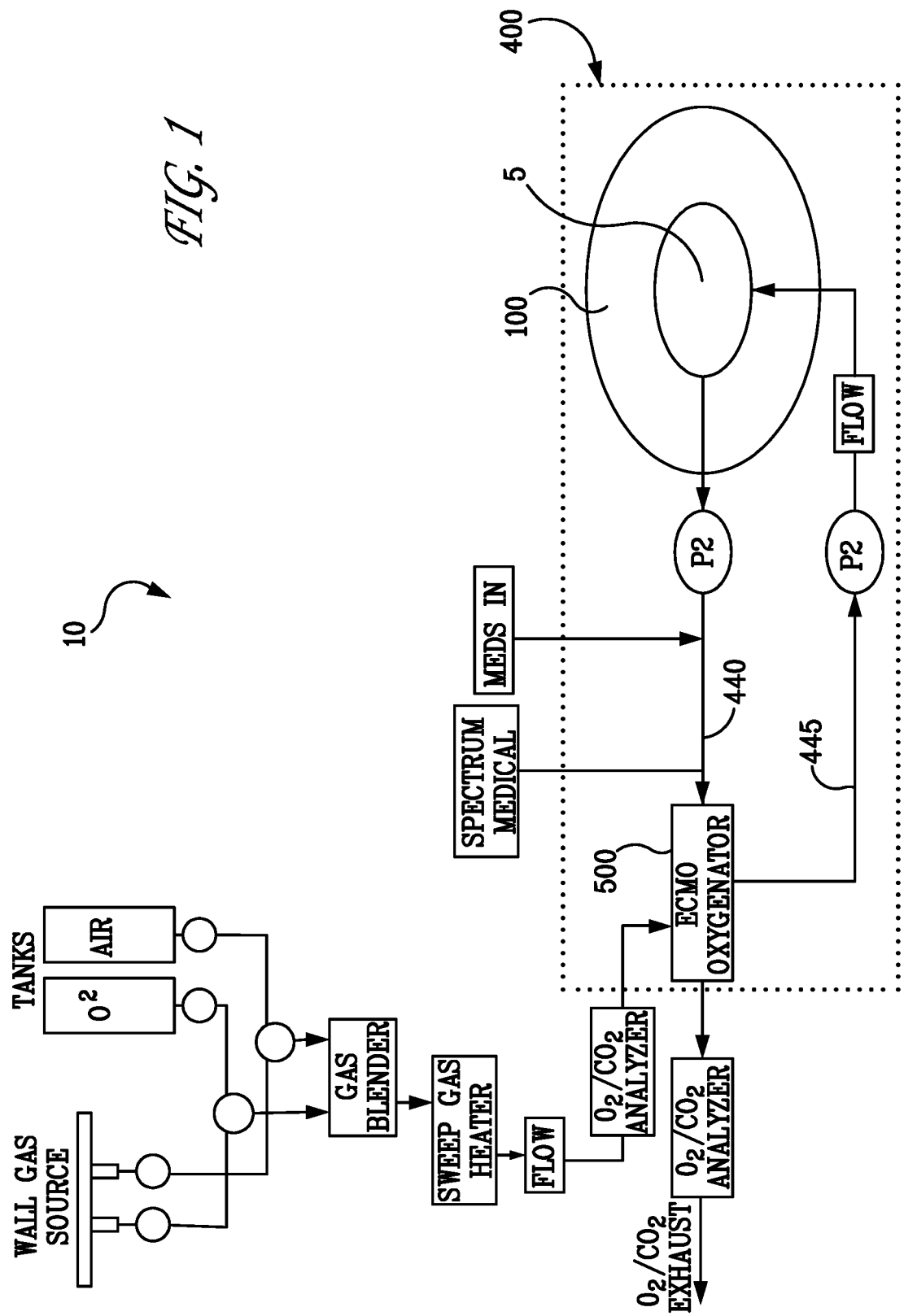
FIG. 1 illustrates a schematic of an extracorporeal support system according to an aspect of the disclosure.
Figure 2:
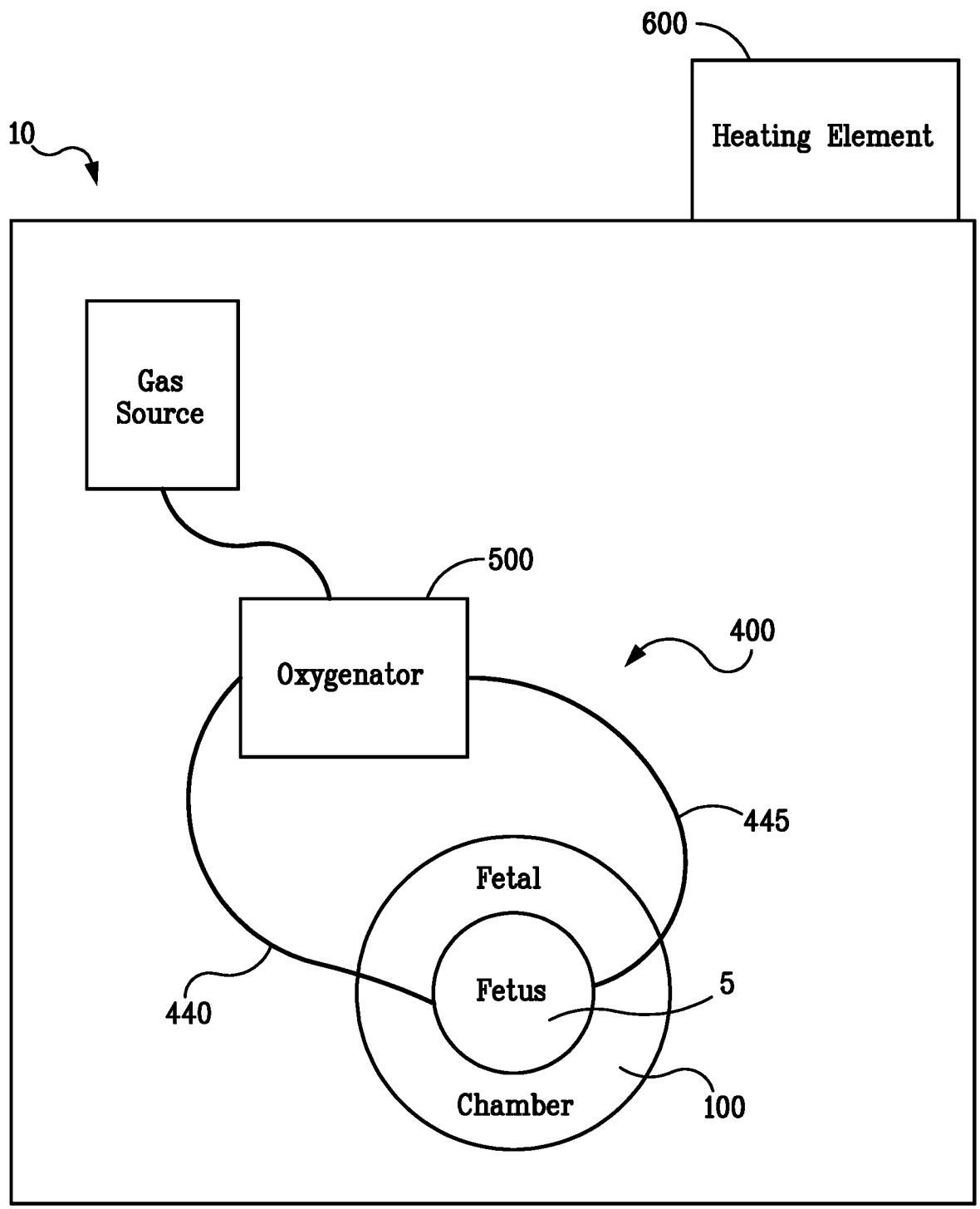
FIG. 2 illustrates a schematic of a portion of an extracorporeal support system according to another aspect of the disclosure.
Figure 3:
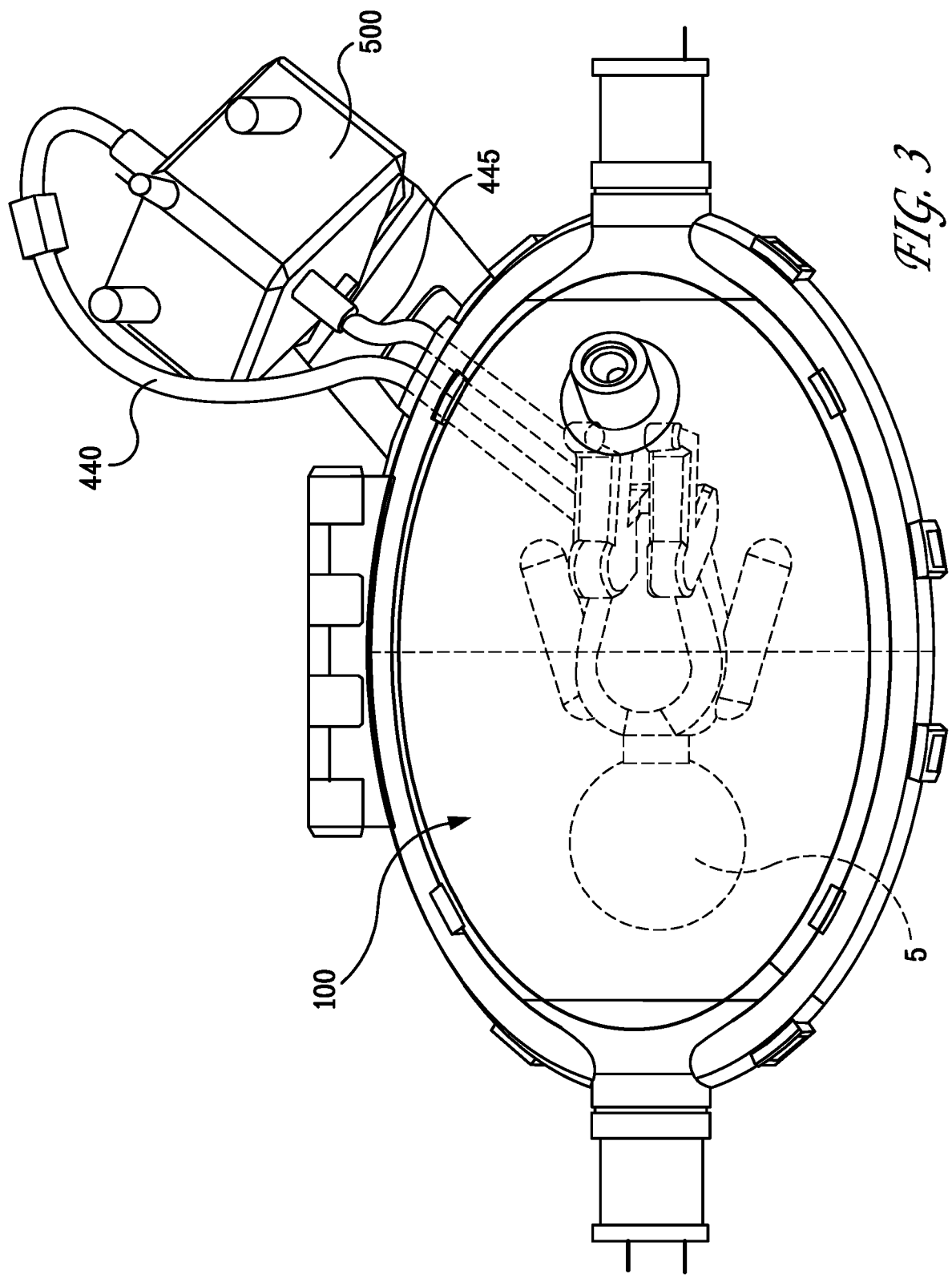
FIG. 3 illustrates an isometric view of a portion of an extracorporeal support system according to yet another aspect of the disclosure.
Figure 4:
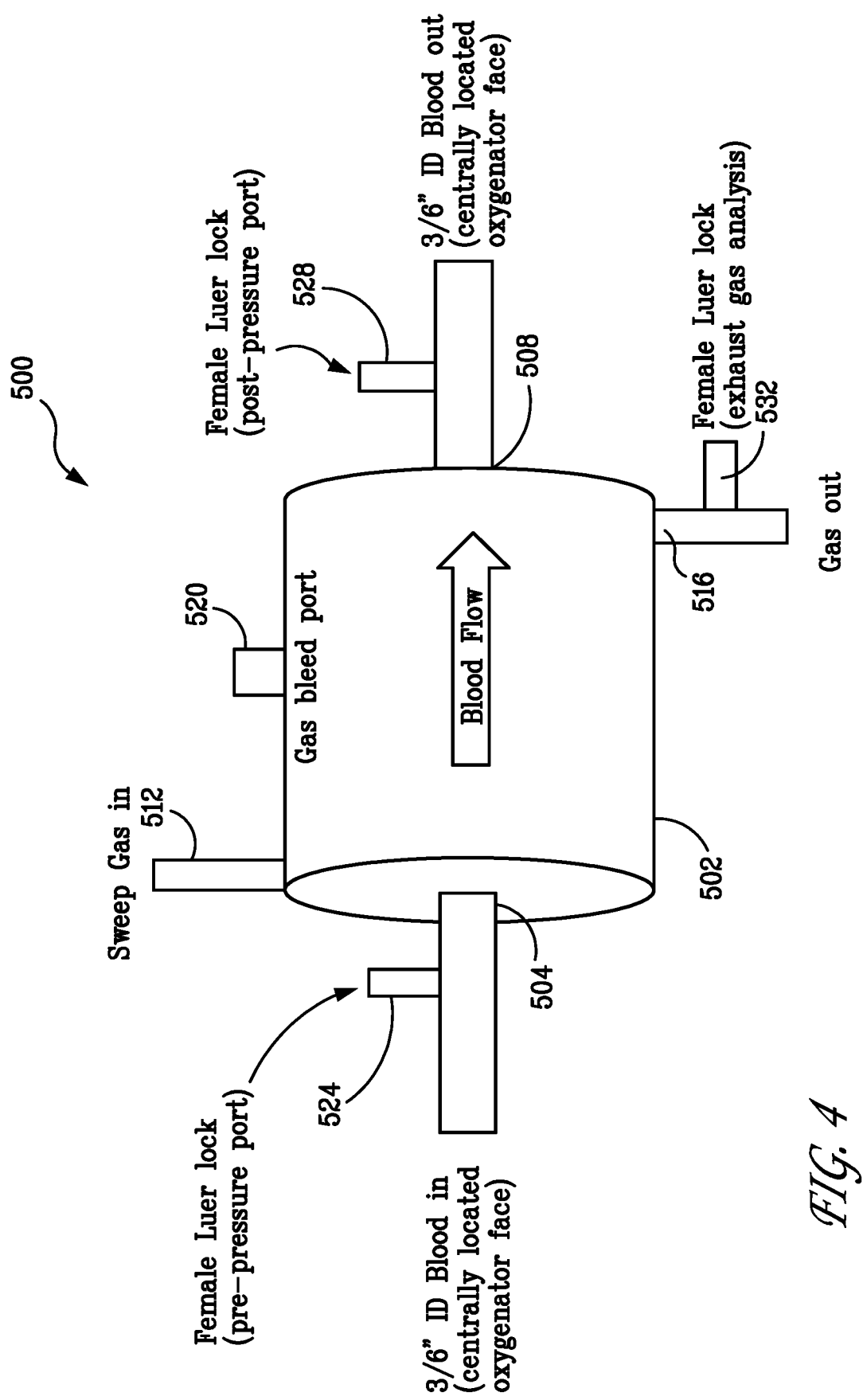
FIG. 4 illustrates an isometric view of an oxygenator according to an aspect of the disclosure.

Referring to FIGS. 1-3, a system 10 is configured to provide extracorporeal support to a premature fetus. According to one aspect of the disclosure, the system 10 may be configured to provide a system environment that is similar to an environment the premature fetus would experience in utero. Viability of a premature fetus that is removed from the uterine environment and that is, for example, between about 22 weeks to about 24 weeks gestation, may be increased by placing the premature fetus in the system environment. According to an aspect of the disclosure, the system environment may be configured to: 1) limit exposure of the premature fetus to light; 2) limit exposure of the premature fetus to sound; 3) maintain the fetus submerged within a liquid environment; 4) maintain the premature fetus within a desired temperature range; or 5) any combination thereof.

The system 10 may be configured to treat preterm or premature fetuses. The preterm fetus may be a premature fetus (for example, less than 37 weeks estimated gestational age, particularly 28 to 32 weeks estimated gestational age), extreme premature fetuses (24 to 28 weeks estimated gestational age), or pre-viable fetuses (20 to 24 weeks estimated gestational age). The gestation periods are provided for humans, though corresponding preterm fetuses of other animals may be used. In a particular embodiment, the preterm fetus has no underlying congenital disease. The term or preterm fetus may have limited capacity for pulmonary gas exchange, for example, due to pulmonary hypoplasia or a congenital anomaly affecting lung development, such as congenital diaphragmatic hernia. In a particular aspect, the subject may be a preterm or term neonate awaiting lung transplantation, for example, due to congenital pulmonary disease (e.g., bronchoalveolar dysplasia, surfactant protein B deficiency, and the like). Such transplantation surgeries are currently rarely performed in the United States. However, the number of transplantation surgeries may be increased with the more stable method for pulmonary support provided by the instant invention. The fetus 5 may also be a candidate for ex utero intrapartum treatment (EXIT) delivery, including patients with severe airway lesions and a long-expected course before definitive resection. The fetus 5 may also be a fetal surgical or fetoscopic procedure patient, particularly with preterm labor precipitating early delivery. According to one aspect of the disclosure, the system 10 may be configured such that the fetus 5 is maintained in the system 10 for as long as needed (for example, for days, weeks or months, until the fetus 5 is capable of life without the system 10). The system 10 should be operable to maintain the fetus 5 for at least 7 days, at least 14 days, at least 21 days, at least 28 days, at least 35 days, at least 42 days, at least 49 days, or at least 56 days.

The system 10 includes a fetal chamber 100 configured to house a fetus 5, an amniotic fluid circuit configured to provide a flow of amniotic fluid to the fetal chamber 100, and an oxygenation circuit 400 configured to remove carbon dioxide from the fetus's blood and supply oxygen to the fetus's blood.

The system 10 is configured to maintain the fetus 5 in the fetal chamber 100 immersed in amniotic fluid. The system 10 is further configured such that the oxygenation circuit 400 provides adequate gas exchange for the fetus 5 to sustain life. In this way, the system 10 provides an environment similar to an intrauterine environment to facilitate continued growth and development of the fetus 5. The system 10 may include a cart or similar device that facilitates monitoring, caring for, and transporting the fetus 5 within a medical facility.

According to an aspect of this disclosure, the system 10 may be as described in U.S. Provisional Patent Application No. 62/434,100, filed on Dec. 14, 2016, the entirety of which is incorporated herein by reference.

The oxygenation circuit 400 can be connected with the fetus 5 in a venous/venous arrangement. Alternatively, the oxygenation circuit 400 may be connected with the fetus 5 in an arterial/venous arrangement. Cannulas may be placed in the great neck vessels (e.g., carotid) of the fetus 5 to connect the circulatory system of the fetus 5 to the oxygenator 500. The placement in the great neck vessels may avoid issues of vasospasm and cannula instability in umbilical vessels. An external portion of the cannulas may be fitted with a sleeve (e.g., to permit increased tension of the stabilizing sutures). The sleeve may be made of silicone and may be, for example, about 1-10 cm in length, particularly about 3-5 cm in length. The cannulas may be sutured to the fetus 5 (for example via the fitted sleeve) to secure the cannulas to the neck of the fetus 5.

In some aspects, the oxygenation circuit 400 may be connected to the fetus 5 via the fetus's umbilical cord. In such an arrangement, cannulas may be sutured into the veins and arteries of the umbilical cord. It will be appreciated that other connection arrangements may be utilized.

The oxygenation circuit 400 may include an oxygenator 500 for providing gas exchange functionality, particularly of oxygen and carbon dioxide, to the fetus 5. The oxygenator 500 can be removably connected to the fetus 5 and, optionally, to other components of the oxygenation circuit 400 and the system 10. The oxygenator 500 is connected with the fetus 5 via two or more fluid lines and includes at least a drain line 440 and an infusion line 445. Blood flows from the fetus 5 though the drain line 440 to the oxygenator 500. The blood then flows through the oxygenator 500 and returns to the fetus 5 via the infusion line 445.

In some aspects, the oxygenator 500 may be configured to be disconnected and replaced while the oxygenation circuit 400 is operational. If the oxygenator 500 is damaged or has surpassed its expected life cycle, the oxygenation circuit 400 may be temporarily configurable to bypass the oxygenator 500 so that the oxygenator 500 may be disconnected from the oxygenation circuit 400 and a new, primed, oxygenator 500 connected in its place.

Referring to FIGS. 4-8, the oxygenator 500 includes a housing 502 that defines a cavity 540 therein. The housing 502 may include a plurality of ports that extend through the housing 502 into the cavity 540. A blood inlet port 504, at which blood from the fetus 5 can enter the oxygenator 500, is disposed on the housing 502. In some aspects, multiple blood inlet ports 504 may be configured to receive, either alternatingly or simultaneously, blood from the fetus 5. The blood inlet port 504 is connected to drain line 440, through which the blood moves from the fetus 5 to the oxygenator 500.

One or more additional ports, such as a pressure transducer 524, may be disposed on or adjacent to the blood inlet port 504 or in-line with the drain line 440. The pressure transducer 524 can measure the pressure of the blood from the fetus 5 that enters the oxygenator 500 at the blood inlet port 504. In some aspects, a sampling port (not shown) may also be disposed on or adjacent to the blood inlet port 504 or the drain line 440 to allow for a portion of the blood entering the oxygenator 500 to be removed from the oxygenation circuit 400 to be analyzed or tested. The sampling port may also be used to inject or infuse medicine or nutrition directly into the blood. The one or more additional ports may have any suitable connection means, such as a Luer connector.

A blood outlet port 508, through which the blood leaves the oxygenator 500 and is returned to the fetus 5, is disposed on the housing 502. The blood outlet port 508 is connected to the infusion line 445, through which the blood moves from the oxygenator 500 to the fetus 5. The number of blood outlet ports 508 may be equal to the number of blood inlet ports 504, or it may be different.

One or more additional ports, such as a pressure transducer 524, may be disposed on or adjacent to the blood outlet port 508 or in-line with the infusion line 445. The pressure transducer 524 can measure the pressure of the blood exiting the oxygenator 500. In some aspects, a sampling port (not shown) may also be disposed on or adjacent to the blood outlet port 508 or the infusion line 445 to allow for a portion of the blood exiting the oxygenator 500 to be removed from the oxygenation circuit 400 to be analyzed or tested. The sampling port may also be used to inject or infuse medicine or nutrition directly into the blood. The one or more additional ports may have any suitable connection means, such as a Luer connector.

A fluid flow meter (not shown) may be positioned in-line with the infusion line 445 to monitor the flow rate of the blood returning to the fetus 5 from the oxygenator 500.

A gas inlet port 512 is disposed on the housing 502 for introducing a sweep gas into the oxygenator 500. The sweep gas may include a single gas or a combination of various gases, for example oxygen and other environmental gases. It will be appreciated that the sweep gas may comprise various ratios of gases that may be adjusted to achieve a desired combination and ratio of gases for use with system 10. In some aspects, the sweep gas may have a flow rate of between about 25 mL/min and about 200 mL/min, between about 50 mL/min and about 175 mL/min, or between about 75 mL/min and about 150 mL/min. In some aspects, the sweep gas flow rate is about 100 mL/min. An additional port (not shown) may be disposed on or adjacent to the gas inlet port 512, and a portion of the sweep gas entering the oxygenator 500 may be removed for analysis or testing. The additional port may have any suitable connection means, such as a Luer connector.

A gas exhaust port 516 is disposed on the housing 502 for emitting the sweep gas from the oxygenator 500. An additional port (not shown) may be disposed on or adjacent to the gas exhaust port 516, and a portion of the sweep gas exiting the oxygenator 500 may be removed for analysis or testing. The additional port may have any suitable connection means, such as a Luer connector.

A gas bleed port 520 may be disposed on the housing 502 for removing excess gas when the oxygenator is filled with fluid.

If the pressure is too great inside the oxygenator 500, the flow of blood into the oxygenator 500 may be obstructed, slowed, or stagnated, which can result in unwanted clotting and/or poor blood circulation for the fetus 5. Unwanted pressure build-up inside the oxygenator 500 may also increase pressure acting on the blood exiting the oxygenator 500 and flowing to the fetus 5. This may increase the flow rate of the blood, which can result in damage to the blood (e.g., to the hemocytes in the blood), leading to unwanted clot formation and decrease blood quality.

In some aspects, the oxygenation circuit 400 is configured such that the blood moves therethrough without actuation from an external pump. Instead, blood is circulated through the drain line 440, the oxygenator 500, the infusion line 445, and any other components by the fetus's heart. That is, the oxygenation circuit 400 is a pumpless circuit. As such, it is advantageous to minimize pressures and resistance within the oxygenation circuit 400, and particularly within the oxygenator 500, so that the blood can be moved therethrough without excess obstruction. The use of a pumpless system avoids exposure of the fetus's heart to excess preload encountered in non-pulsatile pump-assisted circuits. The pumpless system also permits intrinsic fetal circulatory regulation of flow dynamics. The oxygenator 500 preferably has very low resistance, low priming volume, low transmembrane pressure drops, and provides efficient gas exchange. Unwanted pressure build-up in the oxygenator 500, as described above, can also require additional force for moving the blood therethrough. This may put strain on the fetus's heart, leading to health complications. If the heart is unable to overcome the added forces, blood flow may stagnate or slow down significantly, which would lead to stopped or decreased circulation of blood in the fetus.

In some aspects, the oxygenator 500 may have a pressure drop of less than about 50 mmHg, less than about 40 mmHg, or less than about 30 mmHg at 1.5 l/min of blood flow. In some aspects, the fetal pressure may be between about 20 mmHg and 40 mmHg. The priming volume of the oxygenator 500 may be less than about 100 mL, less than about 85 mL, less than about 75 mL, less than about 50 mL, less than about 40 mL, or less than about 30 mL. In some aspects, it may be preferable to have a priming volume between about 20 mL and 50 mL or between about 30 mL and 40 mL. Such a small priming volume is advantageous because it decreases dilution of the fetus's blood with that of the priming material. In some aspects, the oxygenator 500 may have a blood flow range up to about 2.0 l/min, about 2.5 l/min, about 2.8 l/min, or greater. The oxygenator 500 may have a gas transfer rate of about 150 mL/min, about 160 mL/min, about 180 mL/min, or greater for oxygen gas ($O_2$).

The oxygenator 500 includes a gas exchanger 550 disposed within the cavity 540. The blood that enters the cavity 540 at the blood inlet port 504 contacts and flows through and past the gas exchanger 550. The blood then exits the cavity 540 via the blood outlet port 508 on the housing 502. The gas exchanger 550 includes an element configured to allow at least oxygen and carbon dioxide gases to diffuse between the gas exchanger 550 and the blood flowing through the oxygenator 500. The gas exchanger 550 may include a plurality of hollow fibers 554 arranged in a desired pattern, such that the blood may flow past the fibers 554 while contacting the fibers 554. As the blood contacts the fibers 554, diffusion of gases is permitted to occur. It will be appreciated that the rate of diffusion may be predetermined and controlled by various aspects, for example, the composition of the sweep gas, the rate of flow of the blood, the rate of flow of sweep gas, the quantity of the fibers 554, the size and shape of the fibers 554, the relative spacing of the fibers 554 within the oxygenator 500, or by other factors that can affect the above variables.

As shown in FIG. 1, two gases, for example an oxygen source and an air source, can be blended together in a gas blender that blends the oxygen and the air to form the sweep gas. The two gases may be supplied by a high-volume gas reservoir, such as wall lines connected with a central gas supply configured to provide gas to the reservoir. Alternatively, the two gases may be supplied from smaller gas reservoirs, such as a portable oxygen tank and a portable air tank. It will be appreciated that a variety of suitable gases may be used. In some aspects, oxygen and nitrogen gases may be blended to achieve the desired concentration of oxygen. The oxygen concentration may range from 0% to 100% of the blended gas combination.

In some aspects, the fibers 554 comprise polymethylpentene (PMP) due to PMP's desirable qualities of gas permeability. Other suitable gas-permeable materials may be used. Each fiber 554 may have a receiving end 558, at which the sweep gas can enter the fiber 554, and an emitting end 562, from which the sweep gas exits the fiber 554. A channel 566 extends between the receiving end 558 and the emitting end 562 and is configured to carry the sweep gas through the fiber 554.

Figure 8:
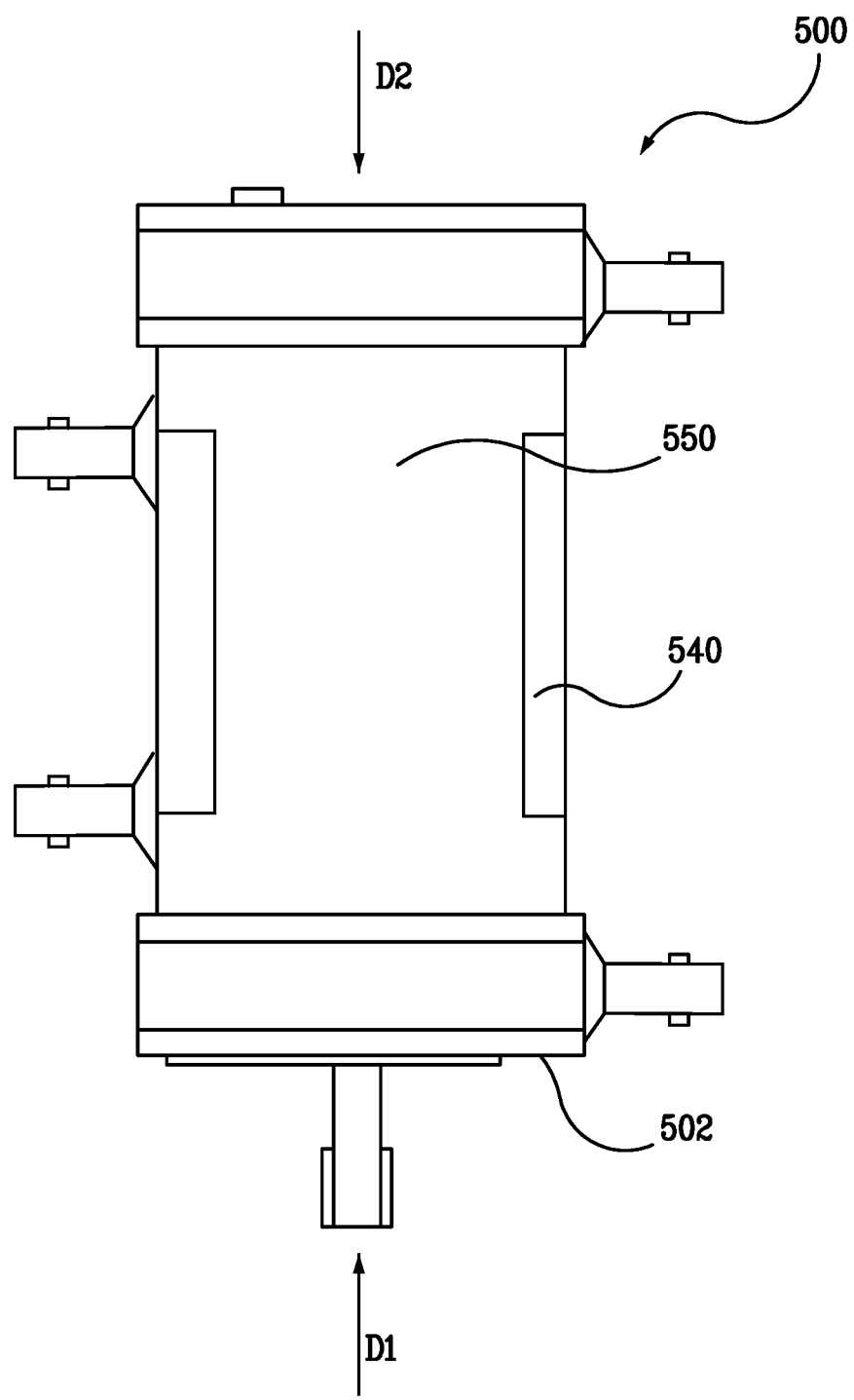
FIG. 8 illustrates a side elevation view of an oxygenator according to an aspect of the disclosure.

The plurality of fibers 554 may be arranged in a specific pattern to comprise the gas exchanger 550. Referring to FIG. 8, in some aspects, the gas exchanger 550 may be substantially cylindrical. Each of the fibers 554 may extend between the top and bottom opposing planar ends of the cylinder, such that all of the fibers 554 are disposed parallel to each other. In such an arrangement, the direction of flow of the sweep gas is preferably opposite the direction of flow of the blood. Referring to FIG. 8, for example, the sweep gas inlet may be disposed at one opposing planar end of the cylinder (e.g. the top end shown in the figure) with the sweep gas exhaust being disposed at the other opposing planar end of the cylinder (e.g. the bottom end shown in the figure), such that the sweep gas flows in direction D2 from the top to the bottom of the cylinder. The blood inlet port 504 can be arranged at the bottom end shown in the figure, and the blood outlet port 508 can be arranged at the top end shown in the figure, opposite the bottom end, such that the blood flows in a direction D1 from the bottom to the top of the depicted cylinder and opposite the flow of the sweep gas. This is advantageous because it allows for better and more efficient gas exchange between the blood and the gas-exchange fibers 554.

Figure 5:
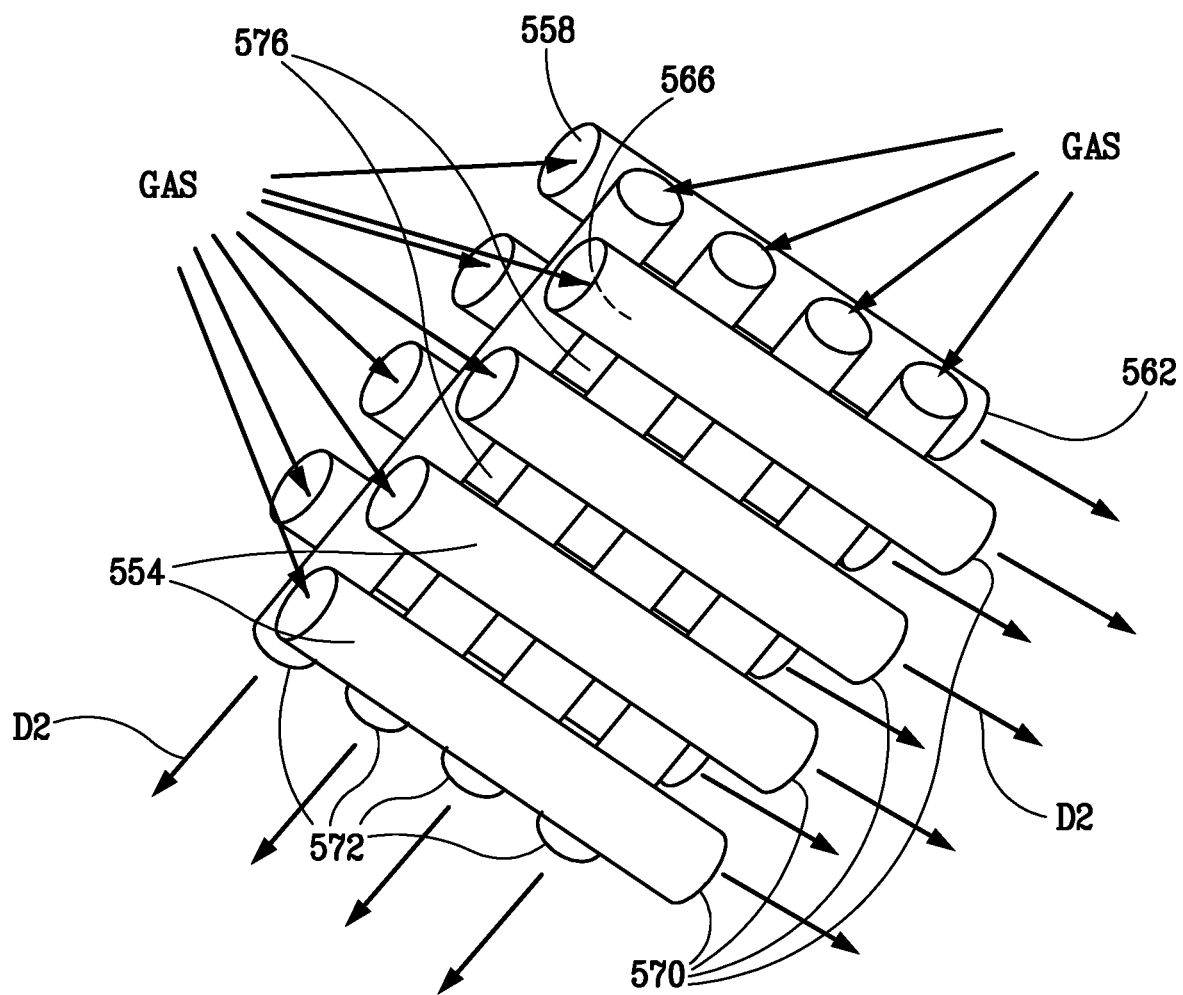
FIG. 5 illustrates an isometric view of a portion of a gas exchanger according to an aspect of the disclosure.
Figure 6:
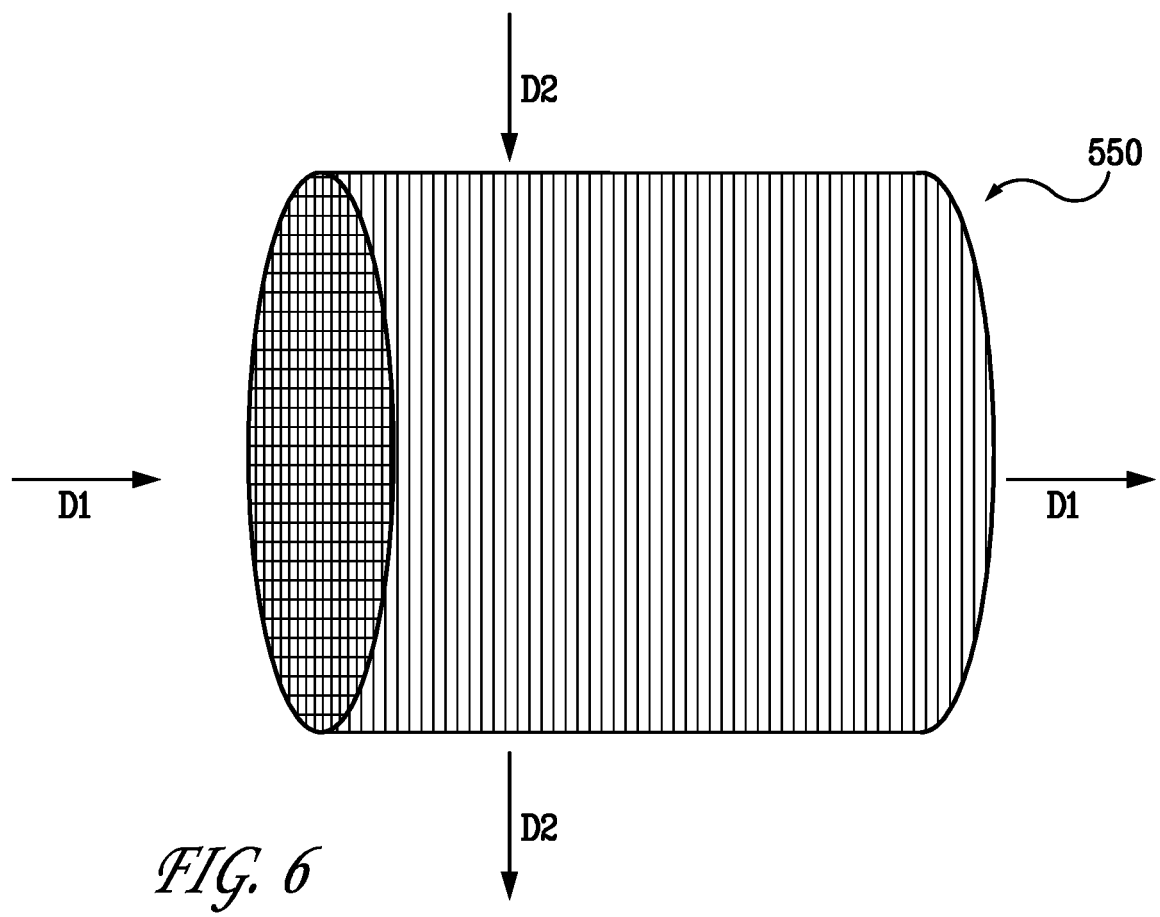
FIG. 6 illustrates an isometric view of a gas exchanger according to another aspect of the disclosure.
Figure 7:
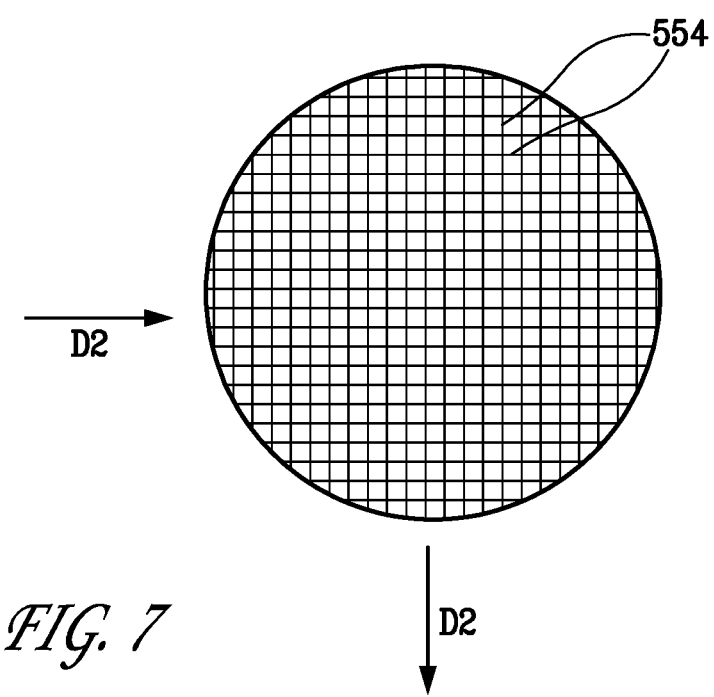
FIG. 7 illustrates a front elevation view of the gas exchanger of FIG. 6.

Referring to FIGS. 5-7, in another aspect of the disclosure, the fibers 554 may be arranged in a crisscross pattern or grid. Multiple fibers 554 may be disposed parallel to each other in a planar arrangement. Multiple such arrangements may make up the gas exchanger 550, and the orientation of each planar arrangement may be the same as another planar arrangement, the same as all other planer arrangements, or different from other planar arrangements. Referring again to FIGS. 5-7, an exemplary portion of a gas exchanger 550 is shown having a first plane 570 that contains a plurality of fibers 554 and a second plane 572 adjacent to the first plane 570. The planes 570 and 572 are substantially the same, except that the fibers 554 of the second plane 572 are perpendicular to the fibers 554 of the first plane 570. While the second plane 572 is shown to be rotated 90 degrees relative to the first plane, it will be appreciated that other relative angles between adjacent planes of fibers may be utilized. Any suitable number of planes 570, 572 may be arranged to form the gas exchanger 550, and the number of planes will depend on the number of fibers 554 desired.

The fibers 554 should be arranged such that a space 576 exists between adjacent fibers to allow the blood to flow through. The size of the space 576 may depend on the quantity of fibers, the flow rate of the blood, the flow rate of the sweep gas, the desired resistance within the oxygenator, or on other parameters that can affect gas exchange of the blood.

The gas exchanger 550 may include various shapes and configurations, such as cylindrical or cuboidal. Referring to FIGS. 6-7, an arrangement of adjacent planes (e.g., plane 570 and plane 572 located at a 90-degree angle to plane 570) may be arranged as a cylinder having two opposing planar ends. Blood can enter the gas exchanger 550 at one of the planar ends, travel through the gas exchanger 550, and exit at the opposite planar end. Sweep gas can enter the gas exchanger 550 at the curved wall of the cylinder at one location and exit at another location on the curved wall.

In some aspects, it may be advantageous to arrange the gas exchanger 550 to have a plurality of planes 570, 572 such that they form a cylinder as described above. Such a gas-exchanger would have a circular cross-section perpendicular to the blood flow direction D. The circular cross-section eliminates corners, thus decreasing areas of higher turbulent flow and helps maintain a constant flow through the gas exchanger 550. This reduces the likelihood of damage to the blood cells and decreases clot formation at areas of higher turbulence (e.g. corners). Such an arrangement may be advantageous because it also decreases pressure within the oxygenator 500 and reduces resistance to flow. As noted above, due to the pumpless nature of the system 10, it is important to have as low resistance to the blood flow as possible to allow the fetal heart to pump blood through the oxygenation circuit 400 without stopping or significantly slowing the flow and without overexerting itself.

In some aspects, the gas exchanger 550, the housing 502, or any of the ports disclosed herein may be coated or lined with anti-clotting materials, such as, but not limited to, immobilized polypeptide and heparin.

The system 10 may include a heating element 600 positioned therein and configured to heat the oxygenation circuit 400. The heating element 600 is not part of the oxygenator 500 itself. The heating element 600 may heat and maintain a desired temperature of the fetus 5, the environment in which the fetus 5 resides, the enclosure of the oxygenation circuit 400, and other components of the system 10. Referring to FIG. 2, an exemplary arrangement is depicted in which the heating element 600 is located separate from the oxygenator 500 and contacts the oxygenation circuit 400. FIG. 2 is an exemplary schematic showing an aspect of such an arrangement, and it will be appreciated that the heating element 600 may be disposed elsewhere and may be either directly adjacent or in indirect contact with the oxygenation circuit 400.

By maintaining the entire oxygenation circuit 400 within the desired temperature, there is no need to additionally heat the blood specifically as it flows to, through, and away from the oxygenator 500. As such, a heating element 600 is neither needed nor desired within the oxygenator 500. Excluding the heating element 600 from the oxygenator 500 allows the oxygenator 500 to be smaller, require fewer fibers 554, and require a smaller amount of priming material to operate. It is important to note that an oxygenator within an extracorporeal circuit generally requires a heating element to maintain the desired temperature of the blood traveling therethrough. Failure to do this may result in damage to the blood, shock to the patient, or other health hazards. In the systems described throughout this application, the above drawbacks are eliminated by heating the entire system 10, or at least the oxygenation circuit 400, with the heating element 600. This allows exclusion of a heater from the oxygenator 500 itself, while maintaining the required temperature of the blood and sweep gas moving between the fetus 5 and the oxygenator 500.

As noted above, removing the otherwise-necessary heater from the oxygenator 500 allows for a smaller gas exchanger 550 and a smaller cavity 540, which in turn allows for a smaller necessary priming volume to operate the oxygenator 500. To start the oxygenation process, the oxygenator 500 must be filled with a suitable priming material. The larger the oxygenator 500, the greater the required minimum volume of priming material. In some aspects, when a premature fetus 5 is connected with the oxygenation circuit 400, the priming material comprises adult human blood (e.g. material blood), fetal blood, or a mixture of adult and fetal blood. Adult blood has different properties from fetal blood, and it is preferred to minimize the impact of these differences. Priming the oxygenator 500 with adult blood results in hemodilution of the blood inside the fetus (i.e., the fetal blood will mix with the adult blood used for priming). The greater the volume of the priming material, the greater the hemodilution. It may be advantageous to minimize the hemodilution within the fetus 5. By excluding a heater from the oxygenator 500 (in lieu of the heating element 600 within the system 10 or the oxygenation circuit 400), the total volume of the oxygenator 500 is decreased, thus requiring a smaller priming volume.

Further, decreasing the total size and volume of the oxygenator 500 also decreases the transit time of the blood as it moves through the oxygenator 500. Increased transit time may lead to thrombosis and clot formation, and decreasing the size of the oxygenator 500, and thus the transit time of the blood flowing therethrough, decreases the chance of clot formation. The blood flow rate through the oxygenator 500 may depend on the age and size of the fetus 5. For example, in some aspects, a neonate weighing approximately 500 grams would have a flow rate of between about 50 mL/min and 60 mL/min. In some aspects, a 24-week-old fetus may have a flow rate of between about 60 mL/min and about 90 mL/min. The flow rate may be higher in a more developed and larger fetus and will depend, in part, on the weight of the fetus. Suitable flow rates may range between about 75 mL/kg/min and about 175 mL/kg/min.

Figure 9:
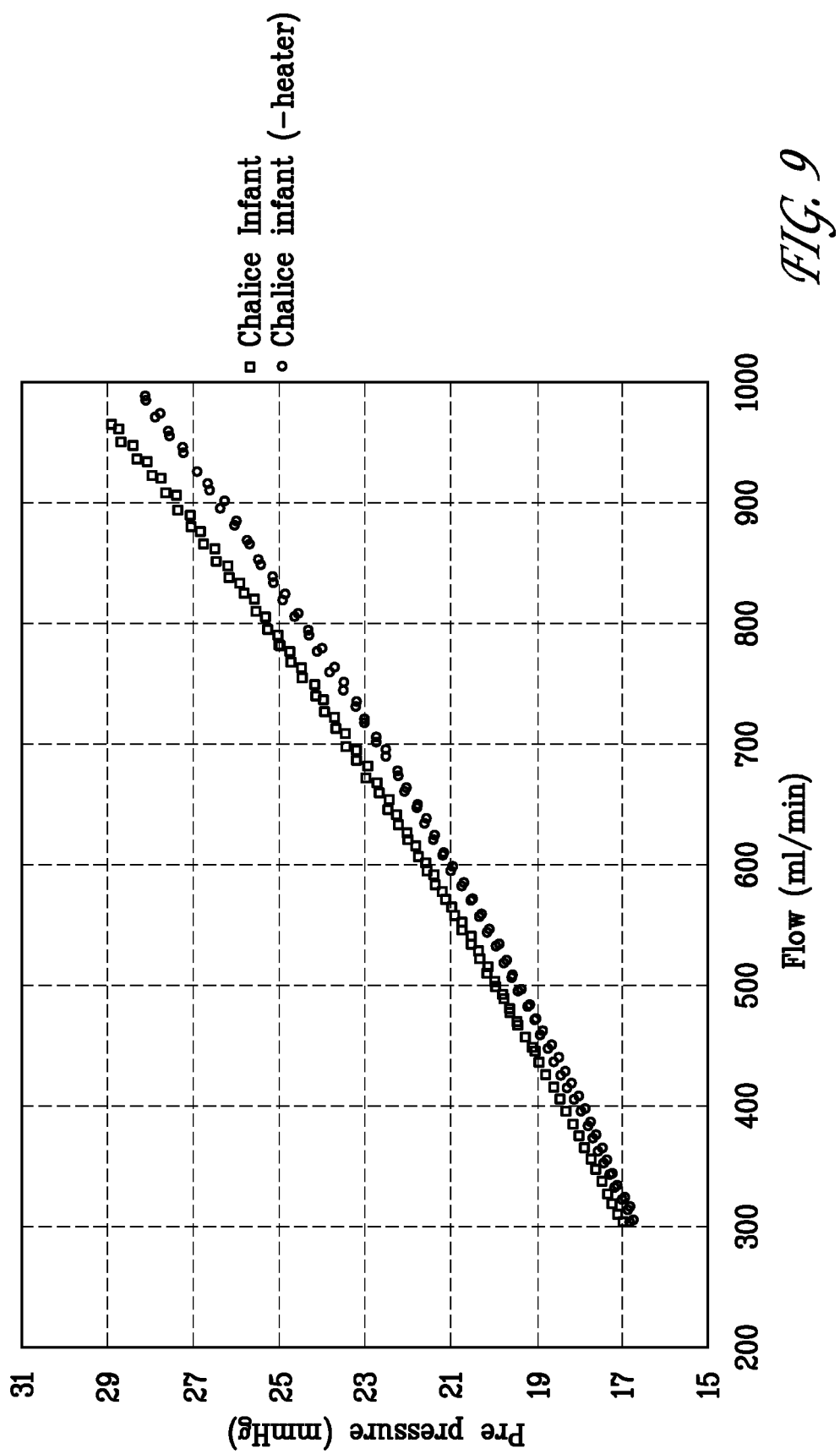
FIG. 9 illustrates a chart comparing pressures over flow between two aspects of oxygenators.

FIG. 9 depicts testing that has been done with embodiments of oxygenators. These findings are not intended to limit the above disclosure, and are used to support the distinctions between oxygenators with built-in heaters and aspects of the oxygenators 500 described throughout this application that are devoid of a heater. Specifically, FIG. 9 depicts differences in pressure measurements between embodiments of oxygenators having heaters and those without heaters.

Various exemplary aspects are described below. Each individual aspect can represent a single aspect of the disclosure, or, alternatively, can be included (either wholly or in part) in one or more aspects. Each aspect can be a stand-alone aspect or be intended to interact with, or be combined with, one or more of any of the other aspects below or otherwise described throughout this application in a preferred combination.

Aspect 1. An oxygenator for use with an extracorporeal circuit, the oxygenator comprising:
  a housing defining a cavity therein, the cavity being configured to receive blood from
  a fetus; and
  a gas exchanger disposed within the interior cavity, the gas exchanger being configured to receive a sweep gas and to contact the blood within the cavity, such that at least oxygen gas and carbon dioxide gas is permitted to diffuse between the blood and the gas exchanger, the gas exchanger including a plurality of fibers,
  wherein each fiber has a receiving end, an emitting end opposite the receiving end, and a channel extending between the receiving end and the emitting end, and
  wherein each fiber is configured to receive a sweep gas at the receiving end and pass the gas through the channel and out of the emitting end.

Aspect 2. The oxygenator of aspect 1, wherein the oxygenator has a direction of flow of blood through the gas exchanger, and each of the plurality of fibers in the gas exchanger is arranged perpendicular to the direction of flow of blood.

Aspect 3. The oxygenator of aspect 1 or 2, wherein the gas exchanger includes a first portion of the plurality of fibers, and wherein each of the first portion of the plurality of fibers are disposed parallel to each other in a first planar arrangement.

Aspect 4. The oxygenator of aspect 3, wherein the gas exchanger includes a second portion of the plurality of fibers, wherein each of the second portion of the plurality of fibers are disposed parallel to each other in a second planar arrangement and perpendicular to the first portion of the plurality of fibers.

Aspect 5. The oxygenator of any of aspects 1 to 4, wherein the gas exchanger is substantially cylindrical having two opposing end planes, and wherein the direction of flow of blood is perpendicular to both of the two opposing end planes of the gas exchanger.

Aspect 6. The oxygenator of aspect 1, wherein:
  the gas exchanger is substantially cylindrical having two opposing end planes;
  the oxygenator has a direction of flow of blood through the gas exchanger; and
  each of the plurality of fibers extends between the two opposing end planes.

Aspect 7. The oxygenator of aspect 6, wherein each of the plurality of fibers in the gas exchanger is arranged parallel to the direction of flow of blood.

Aspect 8. The oxygenator of any of aspects 1 to 7, wherein the oxygenator is devoid of a heating element therein to heat the blood flowing therethrough.

Aspect 9. The oxygenator of any of aspects 1 to 8, wherein the plurality of fibers comprise polymethylpentene (PMP).

Aspect 10. The oxygenator of any of aspects 1 to 9, wherein the oxygenator is pumpless, and the flow of blood is actuated by the fetus.

Aspect 11. The oxygenator of any of aspects 1 to 10, further comprising a gas bleed port configured to release a predetermined amount of the sweep gas from the oxygenator.

Aspect 12. The oxygenator of any of aspects 1 to 11, further comprising a blood inlet port configured to receive blood from the fetus into the oxygenator and a blood outlet port configured to discharge the blood from the oxygenator to the fetus.

Aspect 13. The oxygenator of aspect 12, wherein the blood inlet port includes a pressure transducer configured to measure the pressure of the blood entering the oxygenator.

Aspect 14. The oxygenator of aspects 12 or 13, further comprising a plurality of blood inlet ports.

Aspect 15. The oxygenator of aspect 12, wherein the blood outlet port includes a pressure transducer configured to measure the pressure of the blood exiting the oxygenator.

Aspect 16. The oxygenator of aspect 12 or 15, further comprising a plurality of blood outlet ports.

Aspect 17. The oxygenator of any of aspects 1 to 16, further comprising a gas inlet port configured to receive the sweep gas into the oxygenator.

Aspect 18. The oxygenator of aspect 17, further comprising a gas inlet sampling port configured to allow a portion of the sweep gas to be removed from the gas inlet port.

Aspect 19. The oxygenator of any of aspects 1 to 18, further comprising a gas outlet port configured to emit the sweep gas out of the oxygenator.

Aspect 20. The oxygenator of aspect 19, further comprising a gas outlet sampling port configured to allow a portion of the sweep gas to be removed from the gas outlet port.

Aspect 21. The oxygenator of any of aspects 1 to 20, wherein the sweep gas includes oxygen.

Aspect 22. The oxygenator of any of aspects 1 to 21, wherein the oxygenator is configured to be primed with less than about 100 mL of a priming material.

Aspect 23. The oxygenator of aspect 22, wherein the oxygenator is configured to be primed with less than about 75 mL of the priming material.

Aspect 24. The oxygenator of aspect 23, wherein the oxygenator is configured to be primed with less than about 50 mL of the priming material.

Aspect 25. The oxygenator of aspect 24, wherein the oxygenator is configured to be primed with less than about 40 mL of the priming material.

Aspect 26. The oxygenator of aspect 25, wherein the oxygenator is configured to be primed with less than about 30 mL of the priming material.

Aspect 27. The oxygenator of any of aspects 22 to 26, wherein the priming material comprises human blood.

Aspect 28. The oxygenator of any of aspects 1 to 27, wherein the gas exchanger includes an anticoagulant coating.

Aspect 29. The oxygenator of any of aspects 1 to 28, wherein the oxygenator is configured to maintain a desired functional range of the at least oxygen gas and carbon dioxide gas diffusion for at least 7 days.

Aspect 30. The oxygenator of aspect 29, wherein the oxygenator is configured to maintain the desired functional range for at least 14 days.

Aspect 31. The oxygenator of aspect 30, wherein the oxygenator is configured to maintain the desired functional range for at least 21 days.

Aspect 32. The oxygenator of aspect 31, wherein the oxygenator is configured to maintain the desired functional range for at least 28 days.

Aspect 33. The oxygenator of aspect 32, wherein the oxygenator is configured to maintain the desired functional range for at least 35 days.

Aspect 34. The oxygenator of aspect 33, wherein the oxygenator is configured to maintain the desired functional range for at least 42 days.

Aspect 35. The oxygenator of aspect 34, wherein the oxygenator is configured to maintain the desired functional range for at least 49 days.

Aspect 36. The oxygenator of aspect 35, wherein the oxygenator is configured to maintain the desired functional range for at least 56 days.

Aspect 37. An extracorporeal system for supporting a fetus, the system comprising:
  a chamber configured to receive the fetus;
  an oxygenator operatively connected to the fetus and configured to provide a gas
  exchange to blood from the fetus; and
  a heating element configured to maintain a desired temperature of the system.

Aspect 38. The extracorporeal system of aspect 37, wherein the heating element is separate from the oxygenator.

Aspect 39. The extracorporeal system of aspect 37 or 38, wherein the oxygenator is configured to be removable from the system and replaced with another oxygenator.

While systems and methods have been described in connection with the various embodiments of the various figures, it will be appreciated by those skilled in the art that changes could be made to the embodiments without departing from the broad inventive concept thereof. It is understood, therefore, that this disclosure is not limited to the particular embodiments disclosed, and it is intended to cover modifications within the spirit and scope of the present disclosure as defined by the claims.

What is claimed is:

1. An oxygenator for use with an extracorporeal circuit, the oxygenator comprising:
  a housing defining a cavity therein, the cavity being configured to receive blood from a fetus; and
  a gas exchanger disposed within the cavity, the gas exchanger being configured to receive a sweep gas and to contact the blood within the cavity, such that at least oxygen gas and carbon dioxide gas is permitted to diffuse between the blood and the gas exchanger, the gas exchanger including a plurality of fibers,
  wherein each fiber has a receiving end, an emitting end opposite the receiving end, and a channel extending between the receiving end and the emitting end, and
  wherein each fiber is configured to receive a sweep gas at the receiving end and pass the sweep gas through the channel and out of the emitting end
  wherein the gas exchanger is substantially cylindrical having two opposing end planes; the oxygenator has a direction of flow of blood through the gas exchanger; and
  wherein each of the plurality of fibers extends between the two opposing end planes and is arranged perpendicular to the direction of flow of blood.

2. The oxygenator of claim 1, wherein the gas exchanger includes a first portion of the plurality of fibers, and wherein each of the first portion of the plurality of fibers are disposed parallel to each other in a first planar arrangement.

3. The oxygenator of claim 2, wherein the gas exchanger includes a second portion of the plurality of fibers, wherein each of the second portion of the plurality of fibers are disposed parallel to each other in a second planar arrangement and perpendicular to the first portion of the plurality of fibers.

4. The oxygenator of claim 1, wherein the oxygenator is devoid of a heating element therein to heat the blood flowing therethrough.

5. The oxygenator of claim 1, wherein the plurality of fibers comprise polymethylpentene (PMP).

6. The oxygenator of claim 1, wherein the oxygenator is pumpless, and the flow of blood is actuated by the fetus.

7. The oxygenator of claim 1, further comprising a gas bleed port configured to release a predetermined amount of the sweep gas from the oxygenator.

8. The oxygenator of claim 1, further comprising a blood inlet port configured to receive blood from the fetus into the oxygenator and a blood outlet port configured to discharge the blood from the oxygenator to the fetus.

9. The oxygenator of claim 8, wherein the blood inlet port includes a pressure transducer configured to measure the pressure of the blood entering the oxygenator.

10. The oxygenator of claim 8, further comprising a plurality of blood inlet ports.

11. The oxygenator of claim 8, wherein the blood outlet port includes a pressure transducer configured to measure the pressure of the blood exiting the oxygenator.

12. The oxygenator of claim 1, further comprising a gas inlet port configured to receive the sweep gas into the oxygenator, and a gas inlet sampling port configured to allow a portion of the sweep gas to be removed from the gas inlet port.

13. The oxygenator of claim 1, further comprising a gas outlet port configured to emit the sweep gas out of the oxygenator, and a gas outlet sampling port configured to allow a portion of the sweep gas to be removed from the gas outlet port.

14. The oxygenator of claim 1, wherein the oxygenator is configured to be primed with less than about 100 mL of a priming material.

15. The oxygenator of claim 14, wherein the priming material comprises human blood.

16. The oxygenator of claim 1, wherein the gas exchanger includes an anticoagulant coating.

17. The oxygenator of claim 1, wherein the oxygenator is configured to maintain a desired functional range of the at least oxygen gas and carbon dioxide gas diffusion for at least 7 days.

18. An extracorporeal system for supporting a fetus, the system comprising:
a chamber configured to receive the fetus;
an oxygenator operatively connected to the fetus and configured to provide a gas exchange to blood from the fetus wherein the oxygenator has a priming volume between 20 mL and 50 mL,
the oxygenator comprising a gas exchanger including a plurality of fibers,
wherein the gas exchanger includes a first portion of the plurality of fibers, and wherein each of the first portion of the plurality of fibers are disposed parallel to each other in a first planar arrangement, and
wherein the gas exchanger includes a second portion of the plurality of fibers, wherein each of the second portion of the plurality of fibers are disposed parallel to each other in a second planar arrangement,
wherein each of the first portion of the plurality of fibers and the second portion of the plurality of fibers is arranged perpendicular to a direction of flow of blood within the gas exchanger; and
a heating element configured to maintain a desired temperature of the system.

19. The extracorporeal system of claim 18, wherein the heating element is separate from the oxygenator.

20. The extracorporeal system of claim 18, wherein the oxygenator is configured to be removable from the system and replaced with another oxygenator.

21. The extracorporeal system of claim 18 wherein the oxygenator has a gas transfer rate of about 150 mL/min or greater of oxygen gas.

22. The extracorporeal system of claim 18 wherein the oxygenator is configured to be primed with less than about 100 mL of a priming material comprising human blood.

23. The extracorporeal system of claim 18 wherein the oxygenator is pumpless, and the flow of blood is actuated by the fetus.

24. An oxygenator for use with an extracorporeal circuit, the oxygenator comprising:
a housing defining a cavity therein, the cavity being configured to receive blood from a fetus; and
a gas exchanger disposed within the cavity, the gas exchanger being configured to receive a sweep gas and to contact the blood within the cavity, such that at least oxygen gas and carbon dioxide gas is permitted to diffuse between the blood and the gas exchanger, the gas exchanger including a plurality of fibers,
wherein each fiber has a receiving end, an emitting end opposite the receiving end, and a channel extending between the receiving end and the emitting end,
a first portion of the plurality being fibers disposed parallel to each other and in a first planar arrangement,
a second portion of the plurality of fibers being fibers disposed parallel to each other and in a second planar arrangement,
wherein the oxygenator defines a direction of flow of blood through the gas exchanger, and
wherein each of the first portion of fibers and the second portion of fibers is arranged perpendicular to the direction of flow of blood.

* * * * *